United States Patent [19]
Malfroy-Camine

[11] Patent Number: 5,112,596
[45] Date of Patent: May 12, 1992

[54] METHOD FOR INCREASING BLOOD-BRAIN BARRIER PERMEABILITY BY ADMINISTERING A BRADYKININ AGONIST OF BLOOD-BRAIN BARRIER PERMEABILITY

[75] Inventor: Bernard Malfroy-Camine, Arlington, Mass.

[73] Assignee: Alkermes, Inc., Cambridge, Mass.

[21] Appl. No.: 512,913

[22] Filed: Apr. 23, 1990

[51] Int. Cl.$^5$ .................. G01N 1/00; A61K 37/00
[52] U.S. Cl. ........................... 424/2; 514/17; 514/929
[58] Field of Search .............. 514/17, 929; 424/2

[56] References Cited
FOREIGN PATENT DOCUMENTS
89/09231 10/1989 World Int. Prop. O.

OTHER PUBLICATIONS
Hiesiger, E.M. et al., Annals of Neurology, 19=50-59 (1986).
Barry, D. I. et al., Neurosurgery 10(2)224-6 (1982).
Williams, B. B. et al., J. Infectious Diseases 146(6):819-825 (1982).
Ayre, S. G. Medical Hypothesis 29:283-291 (1989).
Unterberg, A. & Baethmann, A. J., J. Neurosurg., 61:87-96 (1984).
Unterberg et al., J. Cere. Blood Flow and Metab., 4:574-585.
Olsen and Crone, Acta Physiol. Scand., 127:233-241 (1986).
Wahl et al., In: Peptidergic Mechanisms in Cerebral Circulation, 166-190 (1987).
Wahl et al., J. Cere. Blood Flow and Metab., 8:621-634 (1988).
Raymond et al., Can. J. Neuro. Sci., 13:214-220 (1986).
Saria et al., Naunyn-Schniedeberg's Arch. Pharmacol., 324:212-218 (1983).
Kamitani et al., Circulation-Res., 57(4):545-552 (1985).
Unterberg et al., Adv. in Neurosurgery, 13:326-329 (1985).
Schurer et al., Acta Neuropathol., 77:576-581 (1989).
Wahl et al., J. Cere. Blood Flow and Metab., 3:231-237 (1983).
Wahl et al., "Cerebrovascular Effects of Bradykinin", Neural Regulations of Brain Circulation, ed. C. Owman and J. E. Hardebo, Elesevier Science Publ., pp. 419-430 (1986).
Marceau et al., "Pharmacology of Kinins: Their Relevance to Tissue Injury and Inflammation", Gen. Pharmac. 14(2), 209-229 (1983).

Primary Examiner—Glennon H. Hollran
Assistant Examiner—Gary E. Hollinden
Attorney, Agent, or Firm—Hamilton, Brook, Smith & Reynolds

[57] ABSTRACT

The permeability of the blood-brain barrier to endogenous or exogenous neuropharmaceutical or diagnostic agents in an individual's blood stream is increased by administering a bradykinin agonist of blood-brain barrier permeability, such as N-acetyl [Phe$^8$(CH$_2$-NH)Arg$^9$] bradykinin, to the individual. The bradykinin agonist of blood-brain barrier permeability is co-administered with the agent of interest into a blood vessel such as a vein. This co-administration allows the agent of interest to pass the blood-brain barrier into the brain compartment.

16 Claims, 2 Drawing Sheets

ETOH – Ethanol
NAL – Naloxone
BK – Bradykinin
WP – Loperamide
BK+L – Bradykinin and Loperamide
BK+L+N – Bradykinin and Loperamide and Naloxone Cis – Cisplatin
Bk + Cap – Bradykinin and captopril
Bk + Cap + Cis – Bradykinin with captopril and cisplatin Cis – Cisplatin
Cis/Cap + Bk – Cisplatin with captopril and Bradykinin

METHOD FOR INCREASING BLOOD-BRAIN BARRIER PERMEABILITY BY ADMINISTERING A BRADYKININ AGONIST OF BLOOD-BRAIN BARRIER PERMEABILITY

BACKGROUND

As our understanding of the nervous system and its related disorders increases, a wider range of therapeutic and diagnostic agents will become available. Once these agents have been identified, it will be necessary to deliver them to sites of diseased tisssue in the central nervous system. Unfortunately, the existence of the blood-brain barrier limits the free passage of many types of molecules from the blood to cells of the central nervous system.

The physiological basis for the blood-brain barrier is the brain capillaries, which are made of endothelial cells (Goldstein, et al., *Scientific American*, 255: 74–83 (1986); Pardridge, W. M., *Endocrin. Rev.* 7:314–330 (1986)). These endothelial cells are different from those found in other tissues of the body. In particular, they form tight junctions between themselves. The actual blood-brain barrier is formed by these high-resistance tight intercellular junctions which form a continuous wall against the passive movement of molecules from the blood to the brain. These cells are also different in that they have few pinocytotic vesicles, which in other tissues allow somewhat unselective transport across the capillary wall. In addition, continuous gaps or channels running through the cells which would allow unrestrained passage are absent.

One function of the blood-brain barrier is to protect the brain from fluctuations in blood chemistry. However, this isolation of the brain from the bloodstream is not complete. There does exist an exchange of nutrients and waste products. The presence of specific transport systems within the capillary endothelial cells assures that the brain receives, in a controlled manner, all of the compounds required for normal growth and function. The obstacle presented by the blood-brain barrier is that, in the process of protecting the brain, it excludes many potentially useful therapeutic and diagnostic agents.

There are several techniques that either physically break through the blood-brain barrier or circumvent it to deliver therapeutic or diagnostic agents. Among these are intrathecal injections, surgical implants, and osmotic techniques.

Intrathecal injection administers agents directly into the brain ventricles and spinal fluid by puncturing the membranes surrounding the brain. Sustained dosages of agents directly into the spinal fluid can be attained by the use of infusion pumps that are implanted surgically. These spinal fluid delivery techniques are used to treat brain cancers, infections, inflammation and pain, but only penetrate into a minute fraction of the brain due to diffusion gradients and the density of neural tissues.

Clinicians prefer to avoid intrathecal injections because they frequently are ineffective and can be dangerous. Substances injected intrathecally are distributed unevenly, slowly and incompletely in the brain. Since the volume of the spinal fluid is small, increases in intracerebral pressure can occur with repeated injections. Furthermore, improper needle or catheter placement can result in seizure, bleeding, encephalitis and a variety of other severe side effects.

Clinicians also can administer agents that "crack open" the endothelial cells that line the brain capillaries. Dr. Edward Neuwelt at the University of Oregon uses such a system to deliver chemotherapeutics and imaging antibodies to tumors in the brain. (Neuwelt, E. A., Implication of the Blood-Brain Barrier and its Manipulation, Vols 1 & 2, Plenum Press, N.Y. (1989)) This technique involves an arterial injection of up to a 300 milliliter bolus of a 25% mannitol solution. The osmotic differential exerted by the mannitol causes the endothelial cells forming the barrier to shrink, opening gaps between them for a brief period. During this period, the drug is administered into the arterial system and is carried directly into the brain. The osmotic approach demonstrates that once past the barrier, therapeutics can be effectively distributed throughout the brain.

Because of the many risks involved, a 24- to 48-hour period in an intensive care unit is necessary following osmotic treatment. Mannitol can cause permanent damage (including blindness) to the eye. If the barrier is permeable for too long, edema results. Cells of the brain also can be damaged when neurotoxic substances in the blood, not generally accessible to the brain, are able to cross the barrier. Finally, there is a serious incidence of seizures in patients during and after the procedure.

SUMMARY OF THE INVENTION

The present invention pertains to a method of increasing the permeability of the blood-brain barrier of a host to a molecule contained in the host's blood-stream. This method comprises intravenous co-administration to the host of an effective amount of a bradykinin agonist of blood-brain barrier permeability. The molecule to be delivered to the brain can be an endogenous molecule or an exogenous molecule that is co-administered sequentially or simultaneously with the bradykinin agonist.

An advantage of the present invention is that it provides a practical means of increasing the permeability of the blood-brain barrier by the intravenous administration of a bradykinin agonist of blood-brain barrier permeability while co-administering a molecule of therapeutic, prophylactic or diagnostic value. In contrast to osmotic treatment or intrathecal delivery, intravenous injection of a bradykinin agonist of blood brain barrier permeability is significantly less traumatic, does not require surgery and is unlikely to necessitate anesthesia. Furthermore, in contrast to the osmotic techniques which allow entry into the brain of a large variety of molecules present in the blood, including protein, the bradykinin agonist preferentially induces passage through the blood brain barrier of small molecules while passage of large molecules such as albumin is substantially unaffected.

The venous route of administration of a bradykinin agonist of blood-brain barrier permeability offers a number of significant advantages over other routes of administration (subcutaneous or intramuscular injection, as well as the more drastic measures of cortical superfusion or carotid artery injection). First, the vascular system affords a method for providing instant drug action. Second, the intravenous route offers a better control over the rate of administration of drugs; prolonged action can be provided by administering a dilute infusion intermittently or over a prolonged period of time. Third, slow intravenous administration of a drug permits termination of the infusion if sensitivity occurs. Fourth, certain drugs, because of their irritating properties, cause pain and trauma when given by the intramuscular or subcutaneous route and must be given intravenously. Fifth, some drugs cannot be absorbed by any other route; the large molecular size of some drugs prevents absorption by the gastrointestinal route, while other drugs, unstable in the presence of gastric juices, are degraded. Last, the vascular route affords a means of administration for the patient who cannot tolerate fluids and drugs by the gastrointestinal route. This unique technique of delivering therapeutic and diagnostic agents into the brain will improve dramatically and immediately the clinician's ability to understand, diagnose and treat diseases of the central nervous system.

DETAILED DESCRIPTION OF THE INVENTION

Figure 1:
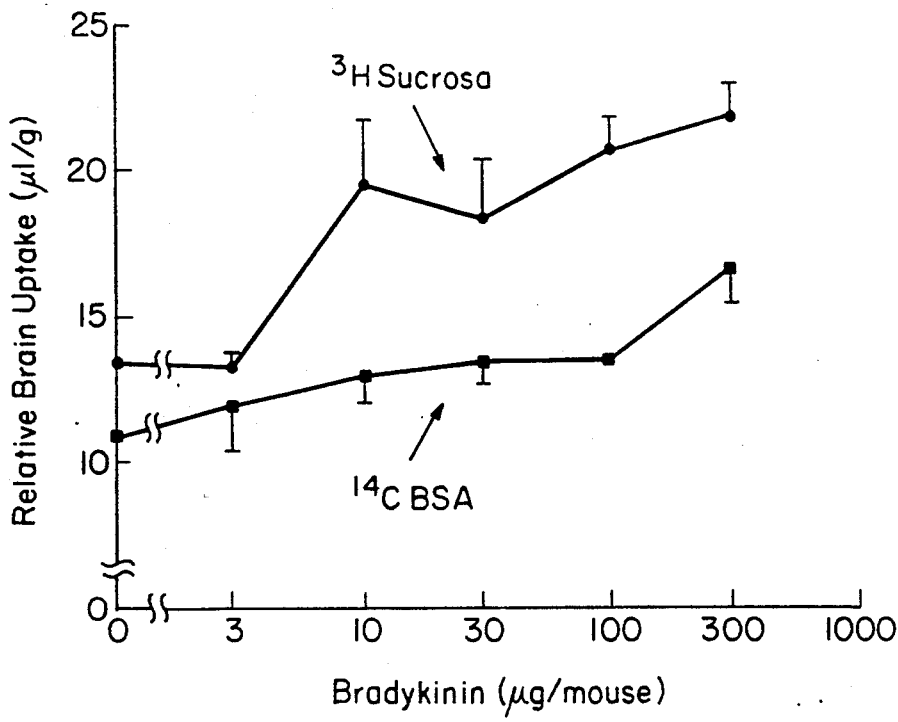
FIG. 1 is a graphic representation of brain uptake (ul/g) of sucrose and BSA co-administered with bradykinin versus dose of bradykinin (ug/mouse).

This invention relates to a method for increasing the permeability of the blood-brain barrier of a host to a molecule present in the host's bloodstream. The host can be any animal which possesses a central nervous system (i.e., a brain). Examples of hosts include mammals, such as humans and domestic animals (e.g. dog, cat, cow or horse), as well as animals intended for experimental purposes (e.g., mice, rats, rabbits).

The molecule in the host's bloodstream can be exogenous to the host. For example, it can be a neuropharmaceutical agent which has a therapeutic or prophylactic effect on a neurological disorder. Examples of neurological disorders include cancer (e.g., brain tumors). Autoimmune Deficiency Syndrome (AIDS), epilepsy, Parkinson's disease, multiple sclerosis, neurodegenerative disease, trauma, depression, Alzheimer's disease, migraine, pain, or a seizure disorder.

Classes of neuropharmaceutical agents which can be used in this invention include antibiotics, adrenergic agents, anticonvulsants, nucleotide analogs, chemotherapeutic agents, anti-trauma agents and other classes of agents used to treat or prevent a neurological disorder. Examples of antibiotics include amphotericin B, gentamycin sulfate, pyrimethamine and penicillin. Examples of adrenergic agents (including blockers) include dopamine and atenolol. Examples of chemotherapeutic agents include adriamycin, methotrexate, cyclophosphamide, etoposide, carboplatin and cisplatin. An example of an anticonvulsant which can be used is valproate and an anti-trauma agent which can be used is superoxide dismutase. Nucleotide analogs which can be used include azido thymidine (AZT), dideoxy Inosine (ddI) and dideoxy cytodine (ddc).

The molecules in the host's bloodstream can also be diagnostic imaging or contrast agents. Examples of diagnostic agents include substances that are labelled with radioactivity, such as 99-Tc glucoheptonate.

The administration of exogenous molecules to the host's bloodstream can be parenterally by subcutaneous, intravenous or intramuscular injection or by absorption through a bodily tissue, such as the digestive tract, the respiratory system or the skin. The form in which the molecule is administered (e.g., capsule, tablet, solution, emulsion) will depend, at least in part, on the route by which it is administered.

The administration of the exogenous molecule to the host's bloodstream and the intravenous injection of bradykinin agonist of blood-brain barrier permeability can occur simultaneously or sequentially in time. For example, a therapeutic drug can be administered orally in tablet form while the intravenous administration of a bradykinin agonist of blood-brain barrier permeability is given 30 minutes later. This is to allow time for the drug to be absorbed in the gastrointestinal tract and taken up by the bloodstream before the agonist is given to increase the permeability of the blood-brain barrier to the drug. On the other hand, the bradykinin agonist of blood-brain barrier permeability can be administered before or at the same time as an intravenous injection of a drug. Thus, the term "co administration" is used herein to mean that the bradykinin agonist of blood-brain barrier and the exogenous molecule will be administered at times that will achieve significant concentrations in the blood for producing the simultaneous effects of increasing the permeability of the blood-brain barrier and allowing the maximum passage of the exogenous molecule from the blood to the cells of the central nervous system.

In addition, the molecule to be delivered to the brain via the host's bloodstream can be endogenous to the host. That is, it can be a biological product that is naturally synthesized and produced by the host. Examples of such biological products include sugars, such as glucose and small peptides, such as enkephalins and thyroid stimulating hormone releasing factor.

Compounds are termed agonists when they increase or elicit a physiological activity. For purposes of this invention, a compound is an agonist of blood-brain barrier permeability when it significantly increases the permeability of the blood-brain barrier for the molecule of interest. This effect is believed to operate through a receptor mediated event. Examples of such compounds include bradykinin and bradykinin analogs. Bradykinin is a naturally occurring peptide comprised of nine amino acids with the following sequence: Arginine-Proline-Proline-Glycine-Phenylalanine-Serine-Proline-Phenylalanine-Arginine (Lehninger, A. L., *Biochemistry*, p. 97, (1975)). An analog is a structural derivative of a parent compound. Analogs of bradykinin can be compounds which are derivatives of the number and/or sequence of amino acids in the bradykinin structure mentioned above which have a similar or enhanced effect on permeability of the blood-brain barrier. Modification of the bradykinin molecule can be done by changing or modifying amino acids, modifying peptide bonds, adding C terminal and/or N-terminal extensions, etc.

A method for preparing bradykinin analogs is Merrifield's procedure of solid-phase peptide synthesis (Merrifield, R. B., *J. Am. Chem. Soc.*, 86:304 (1964); Draprau. G. and Regoli. D., *Methods in Enzymology*, 163: 263–272 (1988)). The first step in a solid-phase synthesis of bradykinin analogs is the formation of a covalent bond between the C-terminal protected amino acid of the chosen peptide sequences and the solid support or resin. The peptide chain is built up residue by residue by repetitive cycles of deprotection, during which the N-terminal Boc-protecting (N-tert-butoxycarbonyl) group is removed by trifluoroacetic acid (TFA). This is followed by neutralization with diisoproplyethylamine (DEA) of the amino group left as a salt and coupling of the next amino acid in the sequence. The cycle is repeated until the sequence is completed. After its complete assembly the peptide is cleaved from the resin and purified.

An effective amount of a bradykinin agonist of blood-brain barrier permeability is that amount which will significantly increase the blood-brain barrier permeability for the molecule of interest. In other words, it will increase the permeability of the blood-brain barrier to allow sufficient quantities of a molecule to pass from the blood to the brain tissue to exert a therapeutic or prophylactic effect or allow diagnostic procedures. The effective amount will be determined on an individual basis and will be based, at least in part, on consideration of the individual's size, the specific disease, the severity of symptoms to be treated, the result sought, the specific bradykinin agonist, the variation of individuals' affinity binding of bradykinin agonists for agonist receptors, etc. Thus, the effective amount can be determined by one of ordinary skill in the art employing such factors and using no more than routine experimentation.

The increase in permeability of the blood-brain barrier in response to a bradykinin agonist relates not only to the quantity of molecules passing from the blood to the brain, but also, to the type of molecule. The effect of bradykinin agonists on blood-brain barrier permeability is to preferentially increase the passage of small molecular weight substances while undisturbing the normal, protective exclusion of the blood-brain barrier to higher molecular weight substances. For example, the data listed in Example 5 demonstrate that the blood-brain barrier permeability of mice to a 40,000 molecular weight molecule was not substantially affected while the permeability to molecules with molecular weights of 1,000 or less was significantly increased. The exact molecular weight limitation for mice is somewhere between about 1,000 and about 40,000 molecular weight. Thus, while the permeability of small molecular weight substances is increased, the normal, protective exclusion of the blood-brain barrier to substances of significantly higher molecular weight is maintained. (See Example V for further detail)

The invention is further illustrated by the following specific examples.

EXAMPLE I

Effect of Intravenously Co-Administered Bradykinin on Brain Tissue Uptake of Sucrose and Bovine Serum Albumin Male Swiss albino mice weighing approximately 20 g were employed. All solutions were prepared in sterile PBS. Intravenous injections (100 ul) were performed in the tail vein. $^3$H-sucrose ($10^6$ cpm) was injected as a bolus without or with bradykinin as stated. Mice were killed at various times after injection. Blood was collected in heparinized tubes and a 100 ul aliquot was subjected to liquid scintillation counting after addition of 1 ml 1% sodium dodecyl sulfate (SDS) to ensure solubilization of proteins. 300 ul 37% hydrogene peroxide as a bleaching agent, and 15 ml Aquasol-2 (Dupont). The brain was removed, homogenized into 5 ml H$_2$O, and 1 ml of the homogenate was aliquoted for liquid scintillation counting (after addition of 1 ml 1% SDS and 15 ml Aquasol.2). Relative brain uptakes were calculated as the ratios of radioactivity recovered in brain over that recovered in blood, and expressed as [radioactivity in 1 g brain]/[radioactivity in 1 ul blood] (ul/g). In some experiemnts, $^{14}$C-BSA ($5 \times 10^5$ cpm) was co-injected together with $^3$H-sucrose ($10^6$ cmp), without or with bradykinin, and the relative brain uptakes of $^{14}$C-BSA and $^3$H-sucrose were calculated after double isotope scintillation counting.

As seen in FIG. 1, the relative brain uptake of $^3$H-sucrose 10 minutes after injection was significantly increased when bradykinin was co-administered with $^3$H-sucrose, at doses of 10, 30, 100 and 300 ug and reached a value of 30 ul/g. The threshold dose of bradykinin was 10 ug, while the two highest doses of 100 and 300 ug yielded almost identical increases in relative brain uptake of $^3$H-sucrose. In contrast, bradykinin at doses of up to 100 ug had no significant effect on the relative brain uptake of $^{14}$C-BSA, which remained between 15 and 18 ul/g.

EXAMPLE II

Pharmacological Characterization of the Effect of Bradykinin on the Mouse Blood-Brain Barrier The protocol for these experiments was the same as described in Example I, except as noted. Drugs were administered to the mice at the concentrations listed in Table 1. Brain levels of $^3$H-sucrose were determined 10 minutes after treatment. The data are derived from two independent experiments except for the desArg$^9$-bradykinin results which were derived from one experiment. Four mice were used for each different drug per experiment. The results are as follows:

TABLE I

| Treatment | Dose/Mouse | N | Brain uptake of sucrose (μl/g) | % Increase |
|---|---|---|---|---|
| None (Control) | | 8 | 100 ± 9 | 0 |
| Bradykinin | 300 μg | 8 | 177 ± 24 | 77 |
| [Phe$^8$(CH$_2$—NH)Arg$^9$]-bradykinin | 125 μg | 8 | 174 ± 15 | 74 |
| N-acetyl[Phe$^8$(CH$_2$—NH)-Arg$^9$]bradykinin | 100 μg | 5 | 230 ± 26 | 130 |
| desArg$^9$-bradykinin | 300 μg | 4 | 90 ± 15 | −10 |

Bradykinin significantly increased the brain uptake of $^3$H-sucrose. In addition, the bradykinin analog and agonist [Phe$^8$(CH$_2$-NH)Arg$^9$]bradykinin, which is specific for B2 receptors, also increased brain uptake. This agonist differs from bradykinin in that the peptide bond between the 8th (Arg) and 9th (Phe) amino acids is replaced with the isoteric CH$_2$-NH bond in order to protect bradykinin from degradation. When this agonist is treated further with N-acetylation to give N-acetyl[-Phe$^8$(CH$_2$-NH)Arg$^9$]bradykinin, the effect on brain uptake is increased to a similar extent as that obtained with bradykinin or the untreated analog. This form of the analog is also devoid of histamine-releasing activity, unlike bradykinin itself. One product of bradykinin degradation is desArg$^9$-Bk. This degradation byproduct results from the action of kininase 1, a proteolytic enzyme, which removes the C-terminal arginine amino acid. This bradykinin analog retains biological activity on $B_1$ receptors, but did not substantially affect the brain uptake of sucrose through the blood-brain barrier.

EXAMPLE III

The Effect of Bradykinin on the Brain Uptake and Analgesic Effect of Loperamide

Tail Flick Assay

Male Swiss albino mice weighing approximately 20 g were again used. The tail flick assay was performed using a Tail Flick Apparatus model TF6 (Emdie Instruments, Maidens, Va.). The intensity of the radiant heat was adjusted to yield a reaction time of between 2 and 3.5 seconds in untreated mice. The cutoff time was set at 7.5 seconds. The tail withdrawal reaction time of mice was measured three times at 10 second intervals immediately prior to intravenous injections. These three values were averages and taken as basal value ($V_0$, ). Another three measurements were taken 10 minutes after intravenous injections and averaged ($V_{10}$). In some experiments, naloxone was administered intraperitoneally 15 minutes (100 ul in sterile PBS, 10 mg/kg) prior to intravenous administration of bradykinin. The results were expressed as percent antinociceptive response according to the formula: $100 \times (V_{10} - V_0)/(7.5 - V_0)$.

Figure 2:
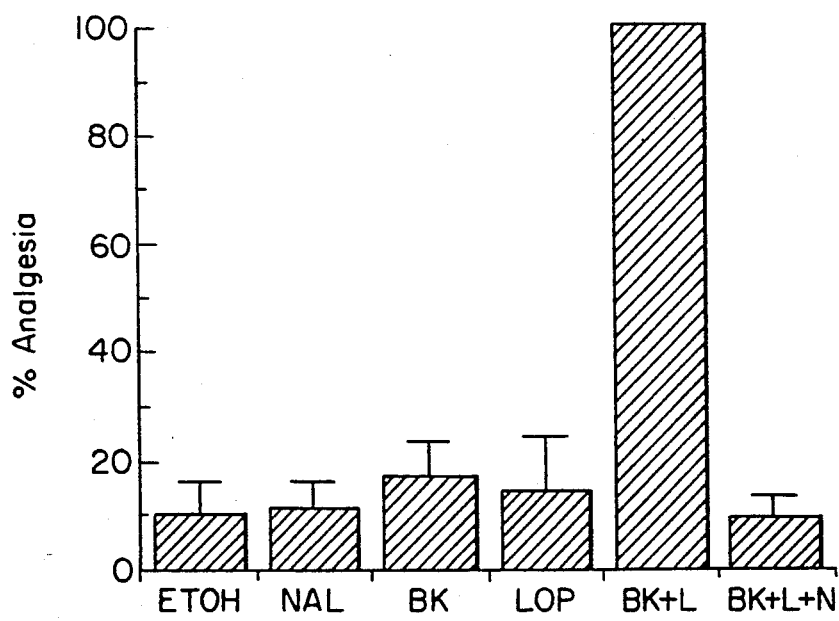
FIG. 2 is a histogram which illustrates the effect of co-administered bradykinin on the antinociceptive activity of Loperamide in the mouse tail flick assay.
Figure 3:
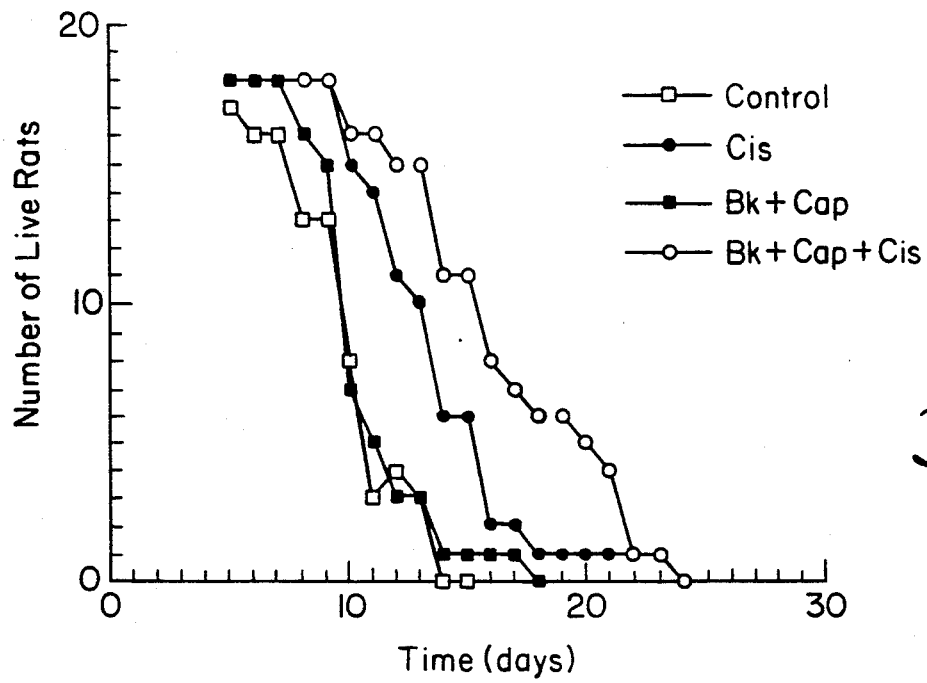
FIG. 3 is a graphic representation of the effects of no treatment (control), treatment with cisplatin, treatment with Captopril and co-administered bradykinin, and treatment with cisplatin, Captopril and co-administered bradykinin in the survival time (days) of rats implanted with a brain tumor, with treatments occuring at days 4 and 6 after tumor implantation.

FIG. 2 illustrates the effectiveness of bradykinin on the brain uptake of loperamide by demonstration of its antinociceptive effect. While loperamide injected intravenously at a dose of 25 ug per mouse had no activity, a complete antinociceptive response was observed when bradykinin (30 ug) was co-injected with the opiate, with the latency of tail withdrawal reaching the cut-off limit of 7.5 seconds in all mice. Pretreatment of mice with naloxone (10 mg/kg) completely antagonized this anticoceptive activity.

EXAMPLE IV

The Effect of the Anti-Tumor Agent Cisplatin When Co-Administered with Bradykinin and Captolpril on the Survival Time of Rate with Brain Tumor Implants Male Fisher rats (200-250 g) were anesthetized with ketamine HCl (100 mg/kg) and acepromazine (10 mg/kg). The animals were placed in a sterotaxic frame. The heads of the animals were shaven and a midline incision was made to expose the skull. A small hole was drilled over the right sensorimotor cortex. Lastly, a 10 ul cell suspension (9 L glioma cells, $2.5 \times 10^6$ cells/ml) was injected over 5 minutes into the right caudate putamen of each animal and the scalp sutured. On days that followed, the animals received treatments as described below. From day 4 until the end, animals were observed daily for signs of failing health. When signs of very poor health were observed (eye hemmorhage, loss of writhing reflex), animals were killed and perfused with paraformaldehyde for subsequent histology to verify the existence of the tumor.

Study A

Figure 4:
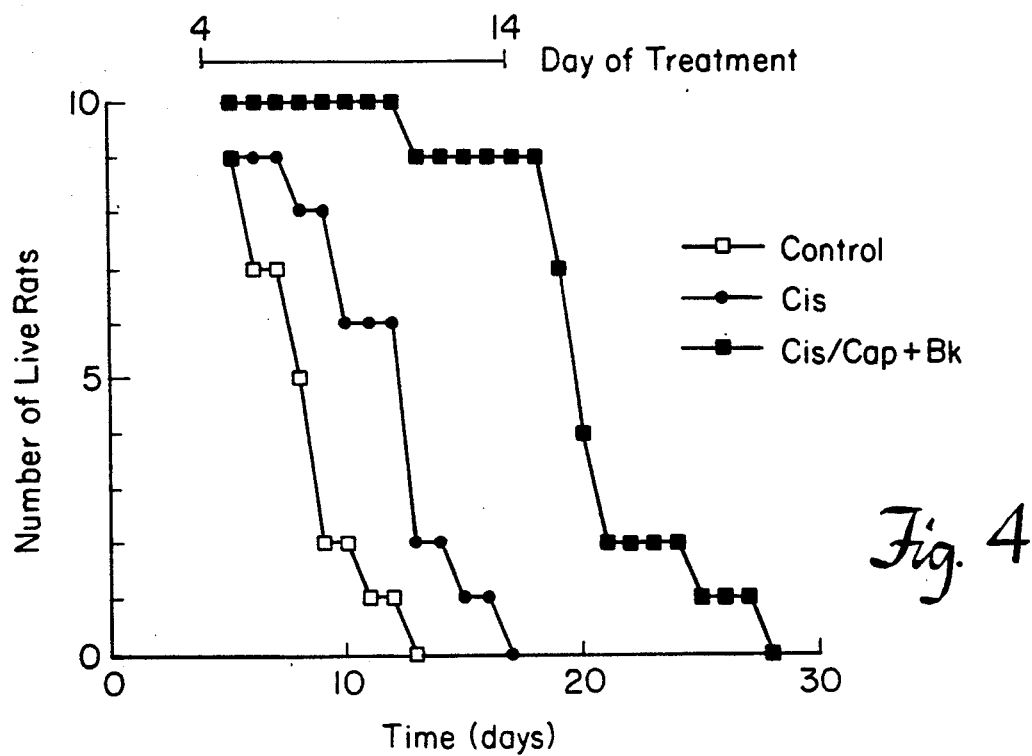
FIG. 4 is graphic representation of the effects of no treatment, treatment with cisplatin and treatment with cisplatin, captopril and co-administered bradykinin on survival time (days) of rats implanted with a brain tumor, with treatment period lasting from day 4 to day 14.

Rats were treated on days 4 and 6 after implantation of the tumor with 600 ug cisplatin i.v. (18 rats, Cis), or 1 mg of Captopril i.p. followed 15 minutes later by 1 mg bradykinin i.v. (18 rats, Cap-Bk), or 1 mg captopril i.p. followed 15 minutes later by 1 mg bradykinin i.v. followed immediately thereafter by 600 ug cisplatin i.v., (18 rats, Cis/cap-bk). Another group of rats received no treatment (17 rats, control). The results are shown in FIG. 4, where survival time versus number of live rats is plotted. Treatment with Captopril plus bradykinin had no effect on survival time. Treatment with the antineoplastic agent, cisplatin, did however significantly increase survival time and pretreatment with Captopril and bradykinin before administering cisplatin augmented significantly this effect. The curves were fitted assuming they follow a Weibull distribution. The mean survival times and corresponding standard deviations are given in the following table in days:

TABLE II

| Group | Mean | S.D. |
| --- | --- | --- |
| Control | 10.0 | 2.37 |
| Cisplatin | 13.1 | 2.90 |
| captopril-Bradykinin | 10.0 | 1.84 |
| Cisplatin/captopril-Bradykinin | 16.5 | 5.77 |

When the anti-tumor agent, cisplatin, was administered alone, the survival time increased from 10.0 to 13.1 days. However, when cisplatin was co-administered with bradykinin and Captopril, the survival time increased even further to 16.5 days. This data suggests that the pretreatment of bradykinin (with captopril to prevent its degradation) increases the blood-brain barrier's permeability to cisplatin and thereby increases the anti-tumor agent's effectiveness in the brain. The Cis/-Cap-Bk group was significantly different statistically from the Cis group with a p value of below 0.025.

Study B

Rats were treated daily from day 4 to day 14 after implantation of the tumor with 200 ug cisplatin i.v. (9 rats, Cis) or 1 mg Captopril i.p. followed 15 minutes later by 1 mg bradykinin i.v. plus 200 ug cisplatin i.v. (10 rats, Cis/Cap-Bk). Another group received Captopril and bradykinin, without cisplatin (9 rats, control). The results are shown in FIG. 5 and confirm the earlier results in Study A which demonstrated that pretreatment with bradykinin and captopril increase significantly the effect of cisplatin on the survival time of rats with brain tumor implants. The mean survivals and corresponding standard deviations are given below in days:

TABLE III

| Group | Mean | S.D. |
| --- | --- | --- |
| Control | 8.1 | 2.05 |
| Cisplatin | 11.9 | 2.62 |
| Cisplatin/captopril-Bradykinin | 19.7 | 2.45 |

The survival times of rats receiving cisplatin with bradykinin and Captopril were significantly higher than rats receiving only cisplatin. The Cis/Cap-Bk group was statistically different from the Cis group with a p value of below 0.005. The increased permeability of the blood-brain barrier caused by the administration of bradykinin (with captopril to prevent its degradation), increased the brain uptake of cisplatin and thereby increased its therapeutic effectiveness.

EXAMPLE V

Effect of Bradykinin on the Brain Delivery of Various Molecules

The protocol for these experiments was the same as described in Example I, except as noted. Drugs (i.e., molecules) were administered intravenously to the mice with or without 300 $\mu$g of bradykinin. Brain levels were determined 10 minutes following treatment. The data are derived from 3 independent experiments. Four mice were used for each different molecule per experiment (N=12). The results were as follows:

TABLE IV

| Molecule | Molecular Wt. Daltons | Increase in Brain Uptake (μl/g) | Percent Increase of Control |
|---|---|---|---|
| Sucrose | 342 | +7.5 + 2.5* | 77 ± 24%* |
| AZT | 267 | +12.3 + 3.0* | 43 ± 10%* |
| Amphotericin B | 1,000 | +2.9 + 0.9* | 24 ± 7%* |
| CD-4 | 40,000 | +1.9 + 1.3 | 19 ± 13% |

*Significantly higher than brain uptake without bradykinin

Bradykinin increases significantly the brain uptake of sucrose, AZT and Amphotericin B. At a molecular weight of 40,000, however, the uptake of CD-4 was not affected. The data indicate that bradykinin preferentially increases the blood-brain barrier permeability to small molecular weight substances while undisturbing its normal permeability to higher molecular weight substances.

Equivalents

Those skilled in the art will recognize, or be able to ascertain using no more than routine experimentation, many equivalents to the specific embodiment of the invention described specifically herein. Such equivalents are intended to be encompassed in the scope of the following claims.

I claim:

1. A method for increasing the permeability of the blood-brain barrier of a host to a neuropharmaceutical or diagnostic agent comprising co-administering intravenously to said host said agent and an effective amount of a bradykinin agonist of blood-brain barrier permeability; said agonist being effective for increasing blood-brain barrier permeability to said agent.

2. A method of claim 1 wherein the host is a human being.

3. A method of claim 2 wherein the bradykinin agonist of blood-brain barrier permeability comprises bradykinin.

4. A method of claim 2 wherein the bradykinin agonist of blood-brain barrier permeability comprises a bradykinin analog.

5. A method of claim 4 wherein said bradykinin analog has significantly increased resistance to proteolytic degradation in the blood stream of the human being relative to bradykinin.

6. A method of claim 1 wherein the bradykinin agonist of blood-brain barrier permeability is selective for bradykinin 2 (B2) receptors.

7. A method of claim 2 wherein the bradykinin agonist of blood-brain barrier permeability and said neuropharmaceutical or diagnostic agent are simultaneously intravenously administered to the host.

8. A method for increasing the permeability of the blood-brain barrier of a host to a therapeutically active agent comprising co-administering intravenously to said host said agent and an effective amount of a bradykinin agonist of blood-brain barrier permeability; said agonist being effective for increasing blood-brain barrier permeability to said agent.

9. A method of claim 8 wherein the bradykinin agonist of blood-brain barrier permeability and said therapeutically active agent are simultaneously intravenously administered to the host.

10. A method of claim 8 wherein the therapeutically active agent in the bloodstream comprises a substance from the group consisting of an antibiotic, an adrenergic agent, a nucleotide analog, a chemotherapeutic agent, an anticonvulsant and an antitrauma agent.

11. A method of claim 10 wherein said antibiotic is amphotericin B.

12. A method of claim 10 wherein said nucleotide analog is azido thymidine.

13. A method of claim 10 wherein said chemotherapeutic agent is cisplatin.

14. A method for increasing the permeability of the blood-brain barrier of a human to a therapeutic or prophylactic agent comprising intravenous co-administration to said human of said agent and an effective amount of a bradykinin agonist of blood-brain barrier permeability, said agonist being effective for increasing blood-brain barrier permeability to said agent.

15. A pharmaceutical composition for intravenous administration to a human for the purpose of increasing the permeability of the blood-brain barrier to a molecule, comprising:
   a) the neuropharmaceutical or diagnostic agent to be delivered from the blood to the brain;
   b) a bradykinin agonist of the blood-brain barrier permeability;
   said agonist being effective for increasing blood-brain barrier permeability to said agent; and
   c) a pharmaceutically acceptable carrier.

16. A method for increasing the permeability of the blood-brain barrier of a host to a neuropharmaceutical or diagnostic agent present in the blood stream of the host comprising administering intravenously to said host an effective amount of a bradykinin agonist of blood-brain barrier permeability under conditions whereby said agent and said agonist are present simultaneously in the blood stream of said host; said agonist being effective for increasing blood-brain barrier permeability to said agent.

* * * * *